United States Patent
Kasvikis

(10) Patent No.: US 8,727,974 B2
(45) Date of Patent: May 20, 2014

(54) ACCESS ASSEMBLY INCLUDING ONE OR MORE COMPRESSIBLE VENTS

(75) Inventor: Dino Kasvikis, Mansfield, MA (US)

(73) Assignee: Covidien LP, Mansfield, MA (US)

(*) Notice: Subject to any disclaimer, the term of this patent is extended or adjusted under 35 U.S.C. 154(b) by 108 days.

(21) Appl. No.: 13/228,937

(22) Filed: Sep. 9, 2011

(65) Prior Publication Data

US 2012/0130190 A1 May 24, 2012

Related U.S. Application Data

(60) Provisional application No. 61/416,777, filed on Nov. 24, 2010.

(51) Int. Cl.
*A61B 1/32* (2006.01)

(52) U.S. Cl.
USPC .................................................... 600/208

(58) Field of Classification Search
CPC ............. A61B 17/3423; A61B 2218/008; A61B 17/3498; A61B 2017/3429
USPC ............ 600/201, 205–208, 219, 184, 187; 604/21, 27, 167.06, 167.01, 167.03, 604/167.07, 164.01
See application file for complete search history.

(56) References Cited

U.S. PATENT DOCUMENTS

| | | | | |
|---|---|---|---|---|
| 5,396,925 A | * | 3/1995 | Poli .............................. | 137/493 |
| 7,052,454 B2 | * | 5/2006 | Taylor ........................... | 600/114 |
| 7,691,120 B2 | | 4/2010 | Shluzas et al. | |
| 7,951,117 B2 | | 5/2011 | Wingardner, III et al. | |
| 8,257,252 B2 | * | 9/2012 | Kleyman ..................... | 600/206 |
| 2006/0161049 A1 | | 7/2006 | Beane et al. | |
| 2010/0081871 A1 | | 4/2010 | Widenhouse et al. | |
| 2010/0081880 A1 | | 4/2010 | Widenhouse et al. | |

(Continued)

FOREIGN PATENT DOCUMENTS

| | | | | |
|---|---|---|---|---|
| EP | 2044889 | * | 4/2009 | ..................... 600/208 |
| EP | 2044889 A1 | | 4/2009 | |

(Continued)

OTHER PUBLICATIONS

European Search Report for corresponding EP11190335 date of mailing is Feb. 28, 2012 (3 pgs).

*Primary Examiner* — Pedro Philogene

(57) ABSTRACT

An access assembly is provided including a tubular member having a proximal end and a distal end, the proximal end in mechanical cooperation with at least one slit seal member configured to create a fluid-tight seal in a first configuration. The access assembly also includes a first ring secured at the proximal end of the tubular member and a second ring secured at the distal end of the tubular member. The at least one slit seal member is configured to create an opening in a second configuration when forces are applied at opposing ends of the first ring.

19 Claims, 7 Drawing Sheets

(56) References Cited

U.S. PATENT DOCUMENTS

| | | |
|---|---|---|
| 2010/0100043 A1 | 4/2010 | Racenet |
| 2010/0114032 A1 | 5/2010 | Widenhouse et al. |
| 2010/0130179 A1* | 5/2010 | Colligan et al. ............ 455/414.1 |
| 2010/0228092 A1* | 9/2010 | Ortiz et al. .................... 600/204 |
| 2010/0234688 A1 | 9/2010 | Carter |
| 2010/0249523 A1 | 9/2010 | Spiegal et al. |
| 2010/0286484 A1 | 11/2010 | Stellon et al. |
| 2010/0298646 A1 | 11/2010 | Stellon et al. |
| 2011/0028891 A1 | 2/2011 | Okoniewski |
| 2011/0124970 A1 | 5/2011 | Kleyman |
| 2011/0166423 A1* | 7/2011 | Farascioni et al. ............ 600/208 |
| 2011/0190590 A1 | 8/2011 | Wingardner, III et al. |

FOREIGN PATENT DOCUMENTS

| | | |
|---|---|---|
| EP | 2095781 A2 | 9/2009 |
| EP | 2281520 A1 | 2/2011 |
| WO | WO03/034908 A2 | 5/2003 |
| WO | WO2010/102641 A1 | 9/2010 |
| WO | WO2011/150159 A1 | 12/2011 |

\* cited by examiner

ACCESS ASSEMBLY INCLUDING ONE OR MORE COMPRESSIBLE VENTS

CROSS REFERENCE TO RELATED APPLICATION

The present application claims the benefit of and priority to U.S. Provisional Application Ser. No. 61/416,777 filed on Nov. 24, 2010, the entire contents of which are incorporated herein by reference.

BACKGROUND

1. Technical Field

The present disclosure relates to an apparatus and method for accessing a body cavity. More particularly, the present disclosure relates to an access assembly including one or more compressible or flexible vents.

2. Background of Related Art

Access assemblies configured for reception through an incision into an abdominal cavity are known, as are methods of inserting the access assemblies therethrough. Traditional access assemblies include a rigid cannula that is received through the tissue of the body wall into the body cavity. Endoscopic, laparoscopic and other suitable instruments may then be directed through a housing on the proximal end of the cannula to access the body cavity in a sealing manner in a variety of electrosurgical procedures.

Electrosurgery involves the application of electricity and/or electromagnetic energy to cut, dissect, ablate, coagulate, seal tissue, or otherwise treat biological tissue during a surgical procedure. Additionally, certain electrosurgical modes invoke the application of electric spark to biological tissue, for example, human flesh or the tissue of internal organs, without significant cutting. The spark is produced by bursts of radio-frequency electrical energy generated from an appropriate electrosurgical generator. Generally, fulguration is used to coagulate, cut or blend body tissue. Coagulation is defined as a process of desiccating tissue wherein the tissue cells are ruptured and dehydrated/dried. Electrosurgical cutting, on the other hand, includes applying an electrical spark to tissue in order to produce a cutting or dividing effect.

Generally, electrosurgery utilizes an energy generator, an active electrode and a return electrode. The energy generator generates an electromagnetic wave (referred to herein as "electrosurgical energy"), typically above 100 kilohertz to avoid muscle and/or nerve stimulation between the active and return electrodes when applied to tissue. During electrosurgery, current generated by the electrosurgical generator is conducted through the patient's tissue disposed between the two electrodes. The electrosurgical energy is returned to the electrosurgical source via a return electrode pad positioned under a patient (i.e., a monopolar system configuration) or a smaller return electrode positionable in bodily contact with or immediately adjacent to the surgical site (i.e., a bipolar system configuration). The current causes the tissue to heat up as the electromagnetic wave overcomes the tissue's impedance, such that smoke is generated at the electrosurgical site.

Moreover, compressible assemblies configured for accessing a body cavity and permitting reception of electrosurgical instruments therethrough in a sealing manner are also known. Such compressible assemblies are composed of silicone, thermoplastic elastomers (TPE), rubber, foam, gel and other compressible materials and are configured to be compressed to facilitate insertion into an incision. Typically, such assemblies are deformed by a surgeon using his/her fingers or with the assistance of a grasping device, i.e., forceps. Compression of the assembly reduces the profile of the assembly, thereby facilitating reception of the assembly into the incision. Upon release of the compressive force, the compressed assembly returns to an uncompressed configuration. In the uncompressed configuration, the access assembly seals the incision into the body cavity. The assembly may have one or more access ports for receiving the electrosurgical instruments therethrough and applying electrosurgical energy to tissue.

Therefore, it would be beneficial to have an access assembly configured to be inserted through tissue, such that surgical instruments may be easily inserted therethrough and such that smoke evacuation may be easily and effortlessly achieved.

SUMMARY

Accordingly, an access assembly is provided. The access assembly includes a tubular member having a proximal end and a distal end, the proximal end in mechanical cooperation with at least one slit seal member configured to create a fluid-tight seal in a first configuration. The access assembly further includes a first ring secured at the proximal end of the tubular member and a second ring secured at the distal end of the tubular member. The at least one slit seal member is configured to create an opening in a second configuration when forces are applied at opposing ends of the first ring.

The first ring is configured to be received external of the tissue, whereas the second ring is configured to be received within a body cavity. The tubular member is configured to be tapered in a first position to facilitate insertion through the tissue and is configured to define a substantially hour-glass shape in a second position.

The at least one slit seal member is configured to act, in the second configuration, as a smoke vent for enabling smoke evacuation from a surgical site. Additionally, the at least one slit seal member is configured to receive, in the second configuration, at least one surgical instrument therethrough.

The proximal end of the tubular member includes a plurality of lumens and the proximal end of the tubular member may include a plurality of slit seal members. The at least one slit seal member may be configured to be in a straight configuration. In an alternative embodiment, the at least one slit seal member may be configured to be in a curved configuration. In yet another alternative embodiment, the at least one slit seal member may be configured as multiple parallel slits of varying lengths.

In another exemplary embodiment, the at least one slit seal member may be configured to be a duckbill protrusion. The proximal end of the tubular member may also include a plurality of duckbill protrusions. In an alternative embodiment, the proximal end of the tubular member includes at least two slit seal members, one configured to be in a straight configuration and one configured to be a duckbill configuration.

Also provided is a method of accessing a body cavity. The method includes the steps of providing a tubular member having a proximal end and a distal end, the proximal end in mechanical cooperation with at least one slit seal member configured to create a fluid-tight seal in a first configuration; providing a first ring secured at the proximal end of the tubular member; and providing a second ring secured at the distal end of the tubular member; wherein the at least one slit seal member is configured to create an opening in a second configuration when forces are applied at opposing ends of the first ring.

In addition, while certain aspects of this disclosure are described as relating to laparoscopic surgery via the abdominal wall, it should be understood that the present invention is equally relevant to, and may be employed in connection with, other types of surgery such as incision-less surgery, whereby access to a body cavity is provided via a natural orifice such as the vagina, anus, mouth, ear, nasal passage, etc.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1A:
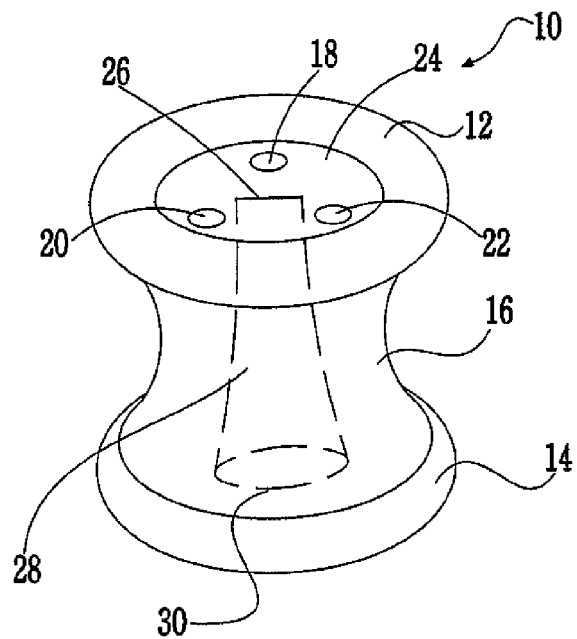
FIG. 1A is a perspective view of an access assembly according to an aspect of the present disclosure, having a slit positioned on a top portion of the access assembly.

The access ports of the present disclosure, either alone or in combination with a cannula assembly, provide a substantially fluid-tight seal between a body cavity of a patient and the outside atmosphere. The access ports, or seal assemblies, of the present disclosure are configured to receive surgical instruments of varying diameter and are also configured to aid in the evacuation of smoke generated at the surgical sites. Various surgical procedures contemplated include laparoscopic and arthroscopic surgical procedures.

The access ports of the present disclosure contemplate the introduction of various types of instrumentation adapted for insertion through a trocar and/or cannula assembly while maintaining a substantially fluid-tight interface about the instrument to help preserve the atmospheric integrity of a surgical procedure from gas and/or fluid leakage. Examples of instrumentation include, but are not limited to, clip appliers, graspers, dissectors, retractors, staplers, laser probes, photographic devices, endoscopes and laparoscopes, tubes, and the like. Such instruments will collectively be referred to as "instruments" or "instrumentation."

Embodiments of the presently disclosed apparatus will now be described in detail with reference to the drawings, in which like reference numerals designate identical or corresponding elements in each of the several views. As used herein, the term "distal" refers to that portion of the tool, or component thereof which is further from the user while the term "proximal" refers to that portion of the tool or component thereof which is closer to the user. While the use of the access assembly is often described herein as engaging an incision, it should be recognized that this is merely exemplary and is not intended to limit the use of the assembly in any way, but rather it should be recognized that the present disclosure is intended to be useable in all instances in situations in which the access assembly engages an incision, a naturally occurring orifice, or any other suitable opening.

Referring initially to FIG. 1A, an assembly for accessing a body cavity is shown generally as access assembly 10. Access assembly 10 is configured to be inserted through an incision or other opening in tissue without excessive handling or manipulation of assembly 10 and without a separate insertion device.

Access assembly 10 includes a first ring 12 (or top ring) and a second ring 14 (or bottom ring). A tubular member 16 having a proximal end and a distal end is positioned between the first ring 12 and the second ring 14. The first ring 12 is secured at the proximal end of the tubular member 16, whereas the second ring 14 is secured at the distal end of the tubular member 16. The proximal end of the tubular member 16 is in mechanical cooperation with at least one slit seal member configured to create a fluid-tight seal in a first configuration, as described below.

Access assembly 10 includes a plurality of lumens or channels. For example, in FIG. 1A, there is illustrated a first channel 18, a second channel 20, and a third channel 22. Each channel 18, 20, 22 may extend the entire length of the access assembly 10. In other words, each channel 18, 20, 22 may extend from the proximal end to the distal end of the tubular member 16.

The top portion 24 of the access assembly 10 also includes a vent or slit 26. Slit 26 is shown centrally located on the top portion 24 of the access assembly 10. However, slit 26 may be positioned in any location relative to the top portion 24 of the access assembly 10. Additionally, the slit 26 may be constructed in a plurality of different shapes and sizes, as will be described below with reference to FIGS. 3A, 4A, 5A. The slit 26 extends the entire portion of the tubular member 16. In other words, the slit 26 extends from the proximal end to the distal end of the tubular member 16. The extension of the slit 26 from the first ring 12 to the second ring 14 forms a channel 28 terminating at an opening 30 of the tubular member 16.

Figure 1B:
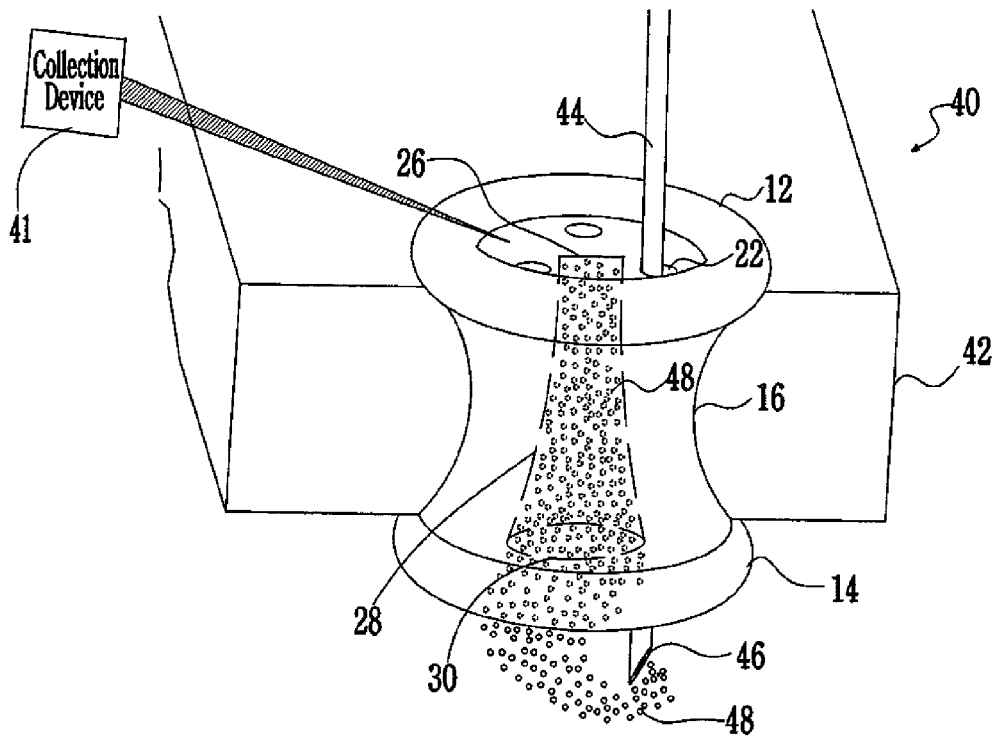
FIG. 1B is a perspective view of the access assembly of FIG. 1 according to an aspect of the present disclosure, where a surgical instrument has been inserted through a channel positioned on the top portion of the access assembly.

Referring to FIG. 1B, operation of the access assembly 10 of FIG. 1A will be described in reference to the channels 18, 20, 22 and the slit 26. In FIG. 1B, access assembly 10 is shown in a second configuration 40 inserted into tissue 42. The first ring 12 is configured to be received external to the tissue 42, whereas the second ring 14 is configured to be received within the body cavity. A surgical instrument 44 is inserted through the third channel 22 and extends the length of the tubular member 16 such that the tip 46 of the surgical instrument 44 exits the bottom portion of the access assembly 10.

When the surgical instrument 44 is turned on, one or more functions may be activated. For example, the surgical instrument 44 may have an electrocautery function for effecting improved hemostasis by heating tissue and blood vessels using thermogenic energy, preferably radiofrequency energy, to cause coagulation or cauterization. Monopolar surgical instruments or devices utilize one electrode associated with a cutting or cauterizing instrument and a remote return electrode, usually adhered externally to the patient. Bipolar instruments utilize two electrodes and the cauterizing current is generally limited to tissue between the two electrodes of a tissue treating portion (e.g., end effector) of surgical instrument 44. During surgery, electrosurgical instrument 44 generally produces an aerosol or plume 48 (typically referred to as "smoke" by surgeons) when organic material (e.g., the tissue of the patient) is being vaporized. The aerosol 48 created by the vaporization of the organic material is offensive and possibly hazardous when inhaled. The aerosol 48 may include gases such as carbon monoxide as well as solids or liquids suspended in the gas. In addition, the aerosol 48 may include virions, which may be infectious. As such, such aerosol or smoke 48 needs to be evacuated from the surgical site. A collection device 41 may be included to collect any and all of the hazardous or infectious gasses released from the surgical site.

According to FIG. 1B, the smoke 48 travels through the opening 30 and travels up the channel 28 toward the slit 26. Thus, the smoke 48 travels the entire length of the tubular member 16 toward the slit 26. As shown in FIG. 2B, described below, a user or surgeon may compress or apply at least one force to the first ring 12 in order to expand the slit 26 to allow evacuation of the smoke 48. By pinching the first ring 12, the slit 26 opens to act as a vent.

Figure 2A:
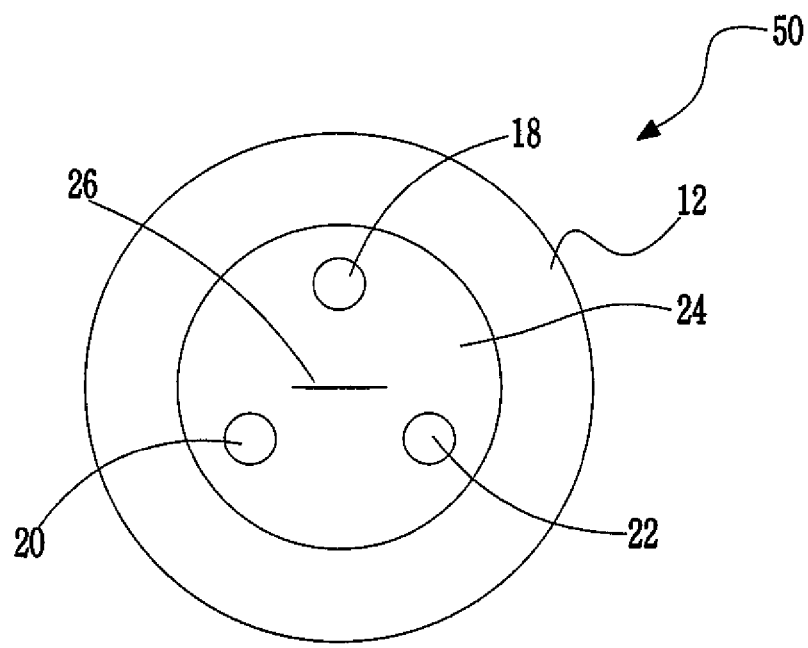
FIG. 2A is a top view of the access assembly of FIG. 1, according to an aspect of the present disclosure, illustrating a plurality of channels and the slit.
Figure 2B:
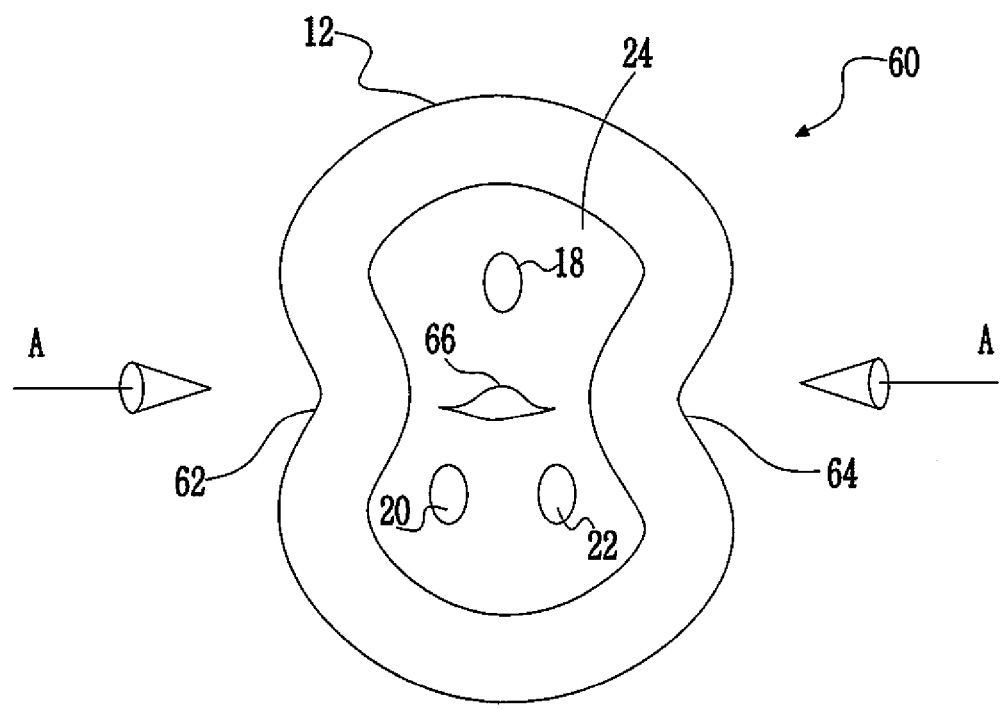
FIG. 2B is a top view of the access assembly of FIG. 2A, according to an aspect of the present disclosure, where at least one force is applied to the top portion of the access assembly to expand the slit.

With reference to FIG. 2A, a top view of the access assembly of FIG. 1, according to an aspect of the present disclosure, illustrating a plurality of channels and the slit is presented. With reference to FIG. 2B, the top view of the access assembly of FIG. 2A, according to an aspect of the present disclosure, where at least one force is applied to the top portion of the access assembly to expand the slit is presented.

In FIG. 2A, the top view 50 depicts the first ring 12 surrounding the top portion 24 of the access assembly 10 (see FIG. 1A). The top portion 24 includes the first channel 18, the second channel 20, the third channel 22, and the slit 26. In this first configuration, the slit 26 is shown in an uncompressed or closed state. As such, without any force applied to the first ring 12, the slit 26 remains closed.

In contrast, in FIG. 2B, the top view 60 depicts the first ring 12 in a second configuration, where at least one force (shown by arrows "A") is applied to the first ring 12 for bending or flexing the first ring 12. The forces may be applied on opposing ends of the first ring 12. As such, the first ring 12 is compressed at portions 62, 64. The compression of the first ring 12 causes the slit 26 of FIG. 2A to expand in a second configuration as an expanded slit 66 in order to, for example, allow the smoke 48 (see FIG. 1B) to exit through the expanded slit 66. Thus, the expanded slit 66 may be selectively used as a vent directly positioned on the top surface 24 of the access assembly 10 (see FIG. 1A). It is contemplated that the expanded slit 66 may be used to accommodate additional surgical instruments, such as smoke removal devices.

Figure 3A:
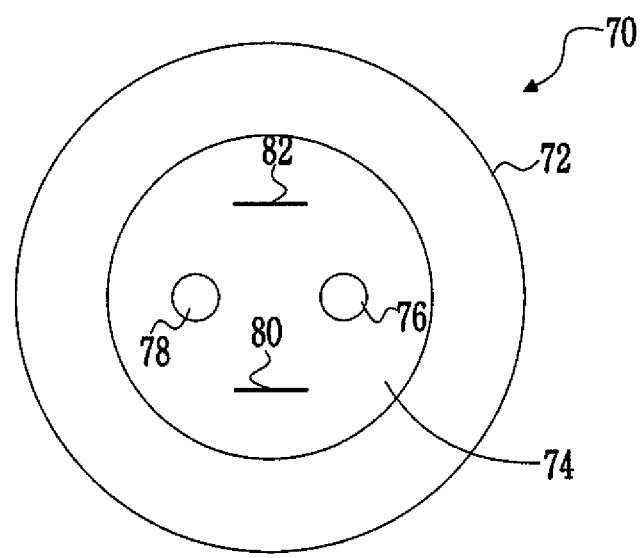
FIG. 3A is a top view of the access assembly, according to an aspect of the present disclosure, illustrating a plurality of channels and a plurality of slits.
Figure 3B:
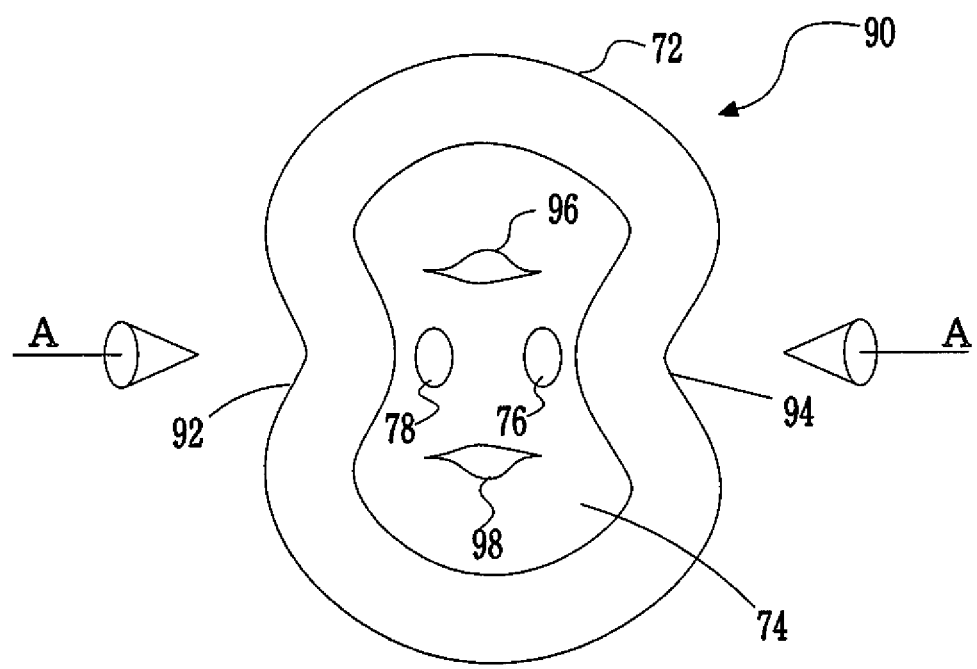
FIG. 3B is a top view of the access assembly of FIG. 3A, according to an aspect of the present disclosure, where at least one force is applied to the top portion of the access assembly to expand the plurality of slits.

With reference to FIG. 3A, a top view of the access assembly, according to an aspect of the present disclosure, illustrating a plurality of channels and a plurality of slits is presented. With reference to FIG. 3B, the top view of the access assembly of FIG. 3A, according to an aspect of the present disclosure, where at least one force is applied to the top portion of the access assembly to expand the plurality of slits is presented.

In FIG. 3A, the top view 70 depicts the first ring 72 surrounding the top portion 74 of an access assembly of a second embodiment of the present disclosure. The top portion 74 includes a first channel 76, a second channel 78, as well as a first slit 80 and a second slit 82. In this first configuration of the second embodiment of the present disclosure, the first and second slits 80, 82 are shown in an uncompressed or closed state. As such, without any force applied to the first ring 72, the first and second slits 80, 82 remain closed.

In contrast, in FIG. 3B, the top view 90 depicts the first ring 72 in a second configuration, where at least one force (shown by arrows "A") is applied to the first ring 72 for bending or flexing the first ring 72. The forces may be applied on opposing ends of the first ring 72. As such, the first ring 72 is compressed at portions 92, 94. The compression of the first ring 72 causes the first and second slits 80, 82 of FIG. 3A to expand in a second configuration as first expanded slit 96 and second expanded slit 98 in order to, for example, allow the smoke 48 (see FIG. 1B) to exit through the first and second expanded slits 96, 98. Thus, the first and second expanded slits 96, 98 may be selectively used as vents directly positioned on the top surface 74 of an access assembly. It is contemplated that the first and second expanded slits 96, 98 may be used to accommodate additional surgical instruments.

Figure 4A:
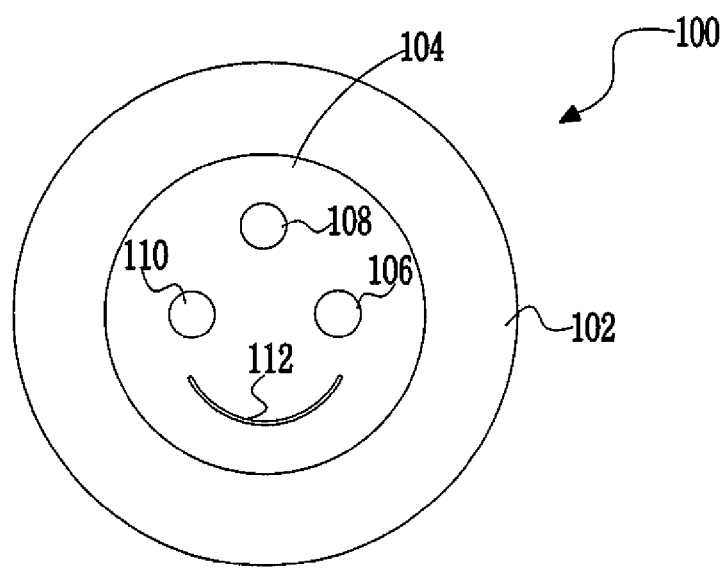
FIG. 4A is a top view of the access assembly, according to an aspect of the present disclosure, illustrating a plurality of channels and a curved slit.
Figure 4B:
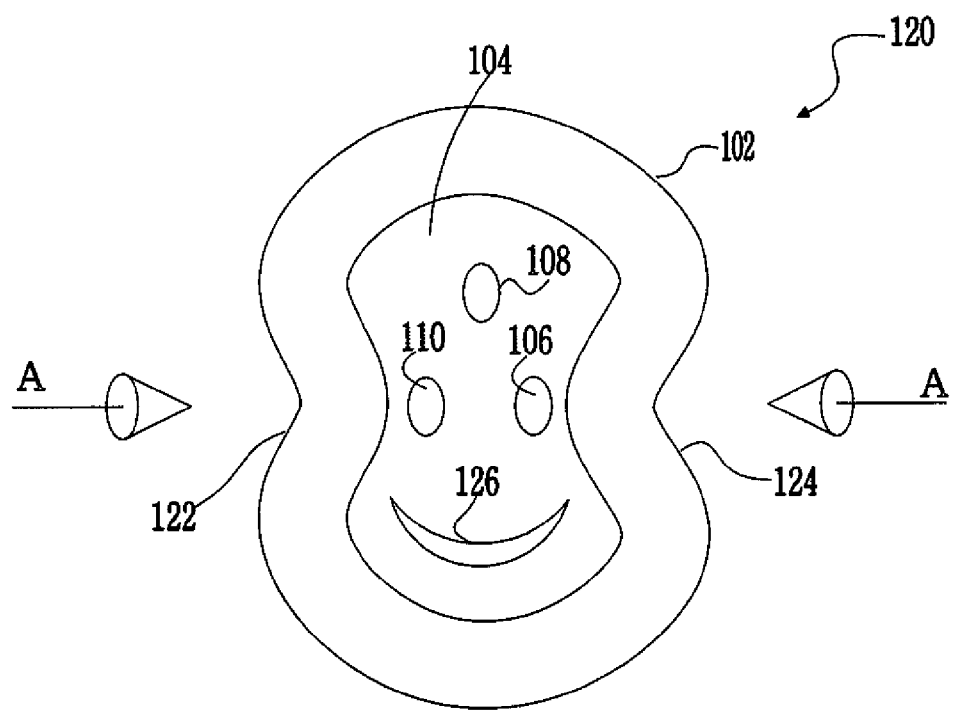
FIG. 4B is a top view of the access assembly of FIG. 4A, according to an aspect of the present disclosure, where at least one force is applied to the top portion of the access assembly to expand the curved slit.

With reference to FIG. 4A, a top view of the access assembly, according to an aspect of the present disclosure, illustrating a plurality of channels and a curved slit is presented. With reference to FIG. 4B, the top view of the access assembly of FIG. 4A, according to an aspect of the present disclosure, where at least one force is applied to the top portion of the access assembly to expand the curved slit is presented.

In FIG. 4A, the top view 100 depicts the first ring 102 surrounding the top portion 104 of an access assembly of a third embodiment of the present disclosure. The top portion 104 includes a first channel 106, a second channel 108, a third channel 110, as well as a curved slit 112. In this first configuration of the third embodiment of the present disclosure, the curved slit 112 is shown in an uncompressed or closed state. As such, without any force applied to the first ring 102, the curved slit 112 remains closed.

In contrast, in FIG. 4B, the top view 120 depicts the first ring 102 in a second configuration, where at least one force (shown by arrows "A") is applied to the first ring 102 for bending or flexing the first ring 102. The forces may be applied on opposing ends of the first ring 102. As such, the first ring 102 is compressed at portions 122, 124. The compression of the first ring 102 causes the curved slit 112 of FIG. 4A to expand in a second configuration as expanded curved slit 126 in order to, for example, allow the smoke 48 (see FIG. 1B) to exit through the curved slit 126. Thus, the curved slit 126 may be selectively used as a vent directly positioned on the top surface 104 of an access assembly. It is contemplated that the curved slit 126 may be used to accommodate additional surgical instruments.

Figure 5A:
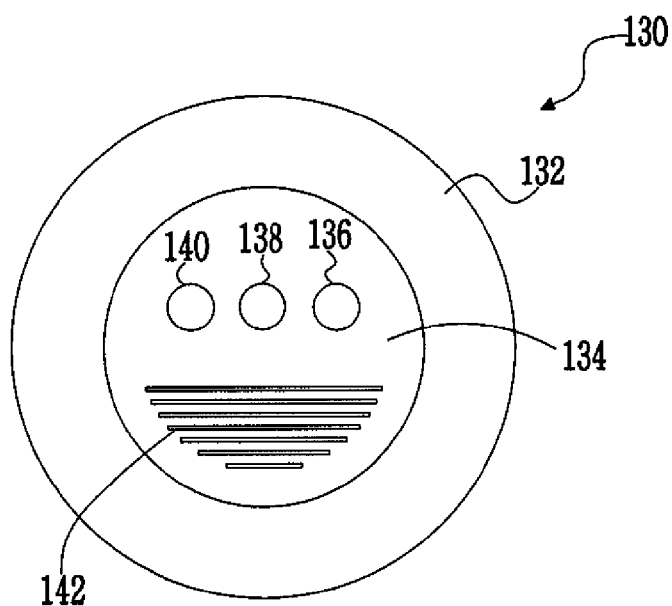
FIG. 5A is a top view of the access assembly, according to an aspect of the present disclosure, illustrating a plurality of channels and a series of parallel slits of varying lengths.
Figure 5B:
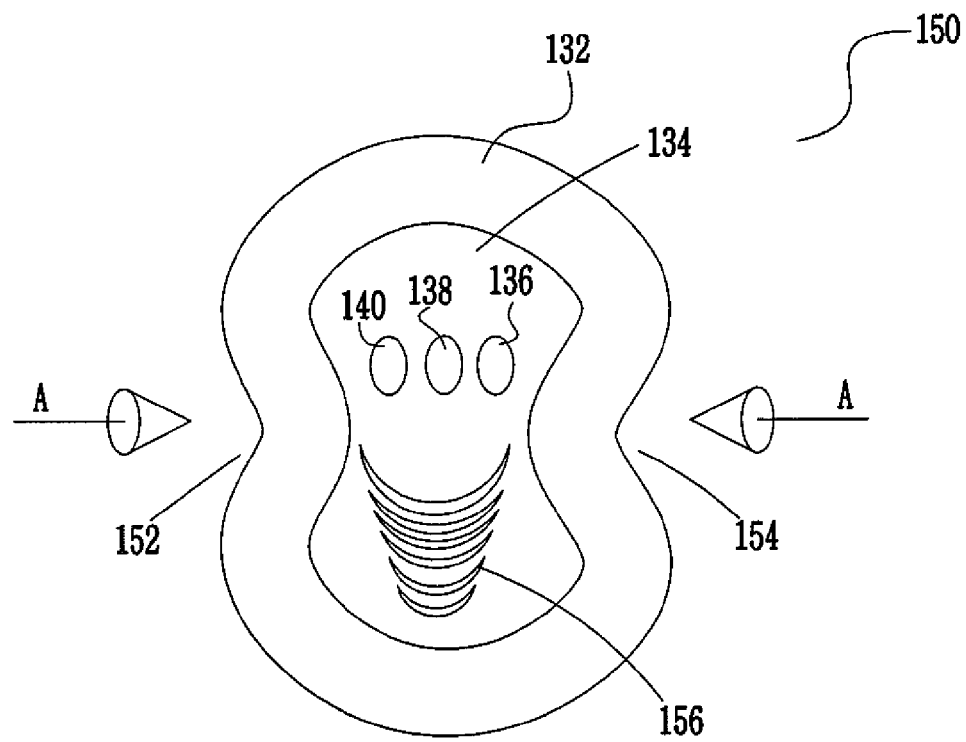
FIG. 5B is a top view of the access assembly of FIG. 5A, according to an aspect of the present disclosure, where at least one force is applied to the top portion of the access assembly to expand the series of parallel slits of varying lengths.

With reference to FIG. 5A, a top view of the access assembly of FIG. 5A, according to an aspect of the present disclosure, where at least one force is applied to the top portion of the access assembly to expand the series of parallel slits is presented. With reference to FIG. 5B, the top view of the access assembly of FIG. 5A, according to an aspect of the present disclosure, where at least one force is applied to the top portion of the access assembly to expand the series of parallel slits is presented.

In FIG. 5A, the top view 130 depicts the first ring 132 surrounding the top portion 134 of an access assembly of a fourth embodiment of the present disclosure. The top portion 134 includes a first channel 136, a second channel 138, a third channel 140, as well as a series of parallel slits 142. The parallel slits 142 may be of the same length or of varying lengths. In this first configuration of the fourth embodiment of the present disclosure, the series of parallel slits 142 are shown in an uncompressed or closed state. As such, without any force applied to the first ring 132, the series of parallel slits 142 remain closed.

In contrast, in FIG. 5B, the top view 150 depicts the first ring 132 in a second configuration, where at least one force (shown by arrows "A") is applied to the first ring 132 for bending or flexing the first ring 132. The forces may be applied on opposing ends of the first ring 132. As such, the first ring 132 is compressed at portions 152, 154. The compression of the first ring 132 causes the series of parallel slits 142 of FIG. 5A to expand in a second configuration as expanded parallel slits 156 in order to, for example, allow the smoke 48 (see FIG. 1B) to exit through the parallel slits 156. Thus, the expanded parallel slits 156 may be selectively used as vents directly positioned on the top surface 134 of an access assembly. It is contemplated that the parallel slits 156 may be used to accommodate additional surgical instruments.

With reference to FIGS. 2A to 5B, described above, it is contemplated that any number of slits may be used in any number of different configurations and in any number of different combinations. The slits may be constructed in any type of shape desirable in order to accommodate additional surgical instruments or in order to allow for the effective evacuation of smoke from a surgical site.

Figure 6A:
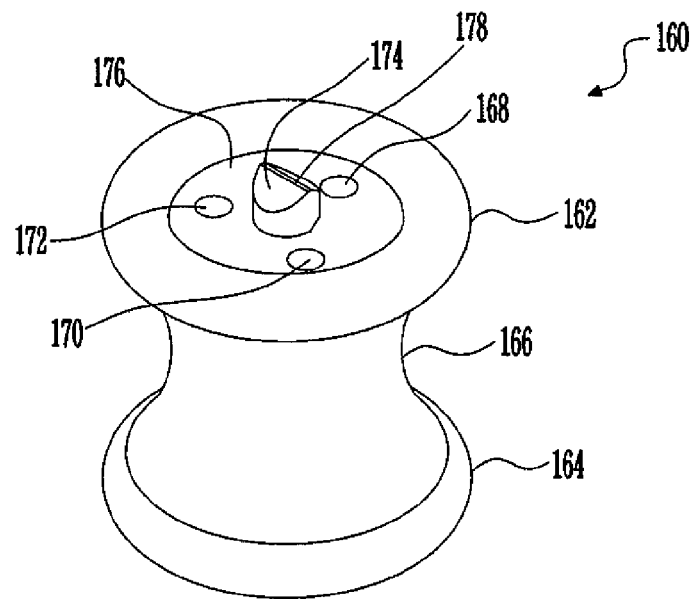
FIG. 6A is a perspective view of an access assembly according to an aspect of the present disclosure, having a duck bill protrusion positioned on the top portion of the access assembly.
Figure 6B:
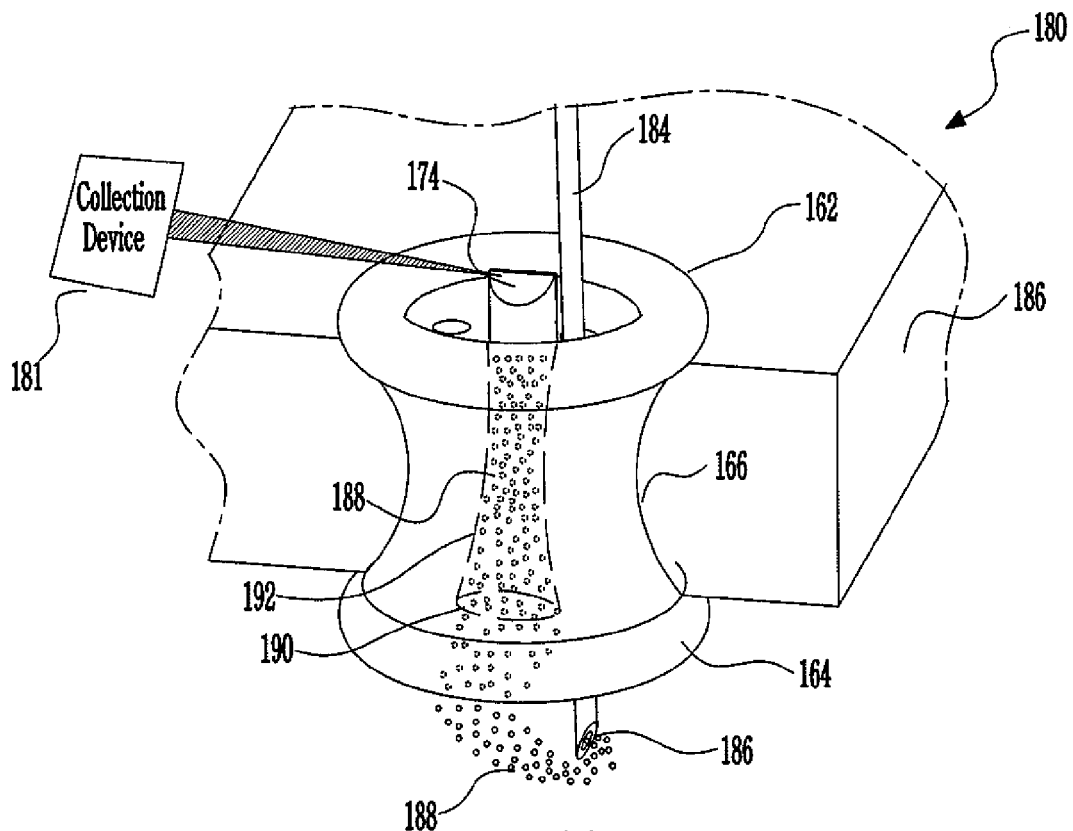
FIG. 6B is a perspective view of the access assembly of FIG. 6A according to an aspect of the present disclosure, where a surgical instrument has been inserted through a channel positioned on the top portion of the access assembly.

Referring to FIG. 6A, a perspective view of an access assembly according to an aspect of the present disclosure, having a duck bill protrusion positioned on a top portion of the access assembly is presented. Referring to FIG. 6B, a perspective view of the access assembly of FIG. 6A according to an aspect of the present disclosure, where a surgical instrument has been inserted through a channel positioned on the top portion of the access assembly is presented.

Access assembly 160 includes a first ring 162 (or top ring) and a second ring 164 (or bottom ring). A tubular member 166 having a proximal end and a distal end is positioned between the first ring 162 and the second ring 164. The first ring 162 is secured at the proximal end of the tubular member 166, whereas the second ring 164 is secured at the distal end of the tubular member 166. The proximal end of the tubular member 166 is in mechanical cooperation with at least one slit seal member or protrusion (having one or more slits incorporated thereon) configured to create a fluid-tight seal in a first configuration, as described below.

Access assembly 160 includes a plurality of lumens or channels. For example, in FIG. 6A, there is illustrated a first channel 168, a second channel 170, and a third channel 172. Each channel 168, 170, 172 may extend the entire length of the access assembly 160. In other words, each channel 168, 170, 172 may extend from the proximal end to the distal end of the tubular member 166.

The top portion 176 of the access assembly 160 also includes a duckbill protrusion 174. Protrusion 174 is shown centrally located on the top portion 176 of the access assembly 160. However, protrusion 174 may be positioned in any location relative to the top portion 176 of the access assembly 160. Additionally, the protrusion 174 may be constructed in a plurality of different shapes and sizes, as will be described below with reference to FIGS. 7A, 7B. The protrusion 174 may include a slit 178 (at the top portion) that extends the entire portion of the tubular member 166. The slit 178 along the width of the protrusion 174 communicates with a lumen extending to the distal end of the tubular member 166.

Referring to FIG. 6B, operation of the access assembly 160 of FIG. 6A will be described in reference to the channels 168, 170, 172 and the protrusion 174 having slit 178. In FIG. 6B, access assembly 160 is shown in a second configuration 180 inserted into tissue 186. The first ring 162 is configured to be received external to the tissue 186, whereas the second ring 164 is configured to be received within the body cavity. A surgical instrument 184 is inserted through the third channel 172 and extends the length of the tubular member 166 such that the tip 186 of the surgical instrument 184 exits the bottom portion of the access assembly 160.

As set forth above, during surgery, electrosurgical instrument 184 generally produces an aerosol or plume 188 (typically referred to as "smoke" by surgeons) when organic material (e.g., the tissue of the patient) is being vaporized, which may be hazardous and which may need to be evacuated from the surgical site. For example, a collection device 181 may be coupled to the protrusion 174 in order to aid in the collection of potentially hazardous gasses.

According to FIG. 6B, the smoke 188 travels through the opening 190 and travels up the channel 192 toward the slit 178 of protrusion 174. Thus, the smoke 188 travels the entire length of the tubular member 166 toward the slit 178 of the protrusion 174. As a result, a user or surgeon may compress or apply at least one force to the first ring 162 in order to expand the slit 178 of the protrusion 174 to allow evacuation of the smoke 188. Slit 178 is opened/closed by pinching or manipulation of protrusion 174.

Figure 7A:
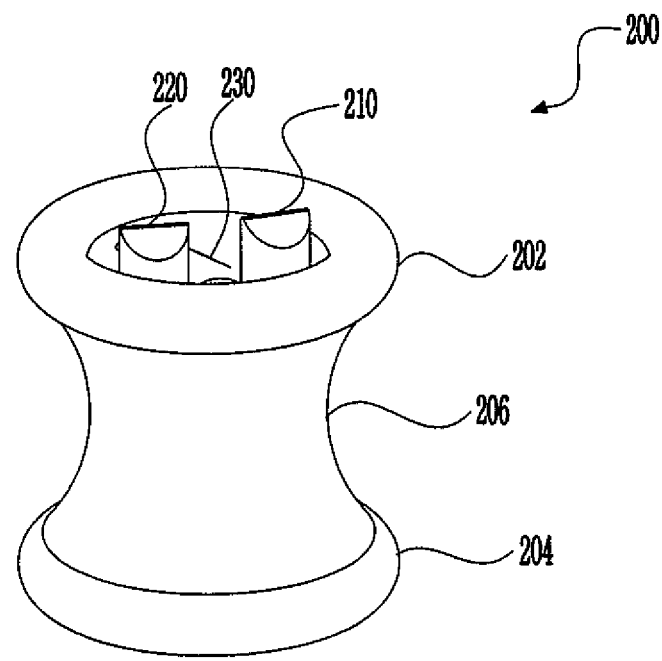
FIG. 7A is a perspective view of an access assembly having both a slit and at least one duck bill protrusion on the top portion of the access assembly.
Figure 7B:
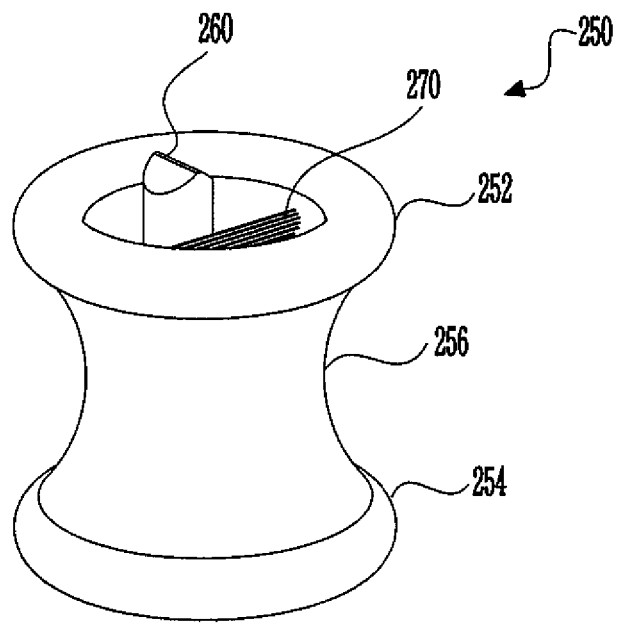
FIG. 7B is a perspective view of an access assembly having both a series of parallel slits and at least one duck bill protrusion on the top portion of the access assembly.

With reference to FIG. 7A, a perspective view of an access assembly having both a slit and at least one duck bill protrusion on a top portion of the access assembly is presented. With reference to FIG. 7B, a perspective view of an access assembly having both a series of parallel slits and at least one duckbill protrusion on the top portion of the access assembly is presented.

In FIG. 7A, access assembly 200 includes a first ring 202 (or top ring) and a second ring 204 (or bottom ring). A tubular member 206 having a proximal end and a distal end is positioned between the first ring 202 and the second ring 204. The first ring 202 is secured at the proximal end of the tubular member 206, whereas the second ring 204 is secured at the distal end of the tubular member 206. Access assembly 200 includes a first protrusion 210 and a second protrusion 220. Access assembly 200 also includes a slit 230. Therefore, it is contemplated to construct access assemblies having a combination of slits and protrusions. The slits and protrusions may be constructed in a plurality of different shapes and sizes.

In FIG. 7B, in an alternative embodiment of the present disclosure, access assembly 250 includes a first ring 252 (or top ring) and a second ring 254 (or bottom ring). A tubular member 256 having a proximal end and a distal end is positioned between the first ring 252 and the second ring 254. The first ring 252 is secured at the proximal end of the tubular member 256, whereas the second ring 254 is secured at the distal end of the tubular member 256. Access assembly 250 includes a protrusion 260 and a series of parallel slits 270. The parallel slits 270 may be of the same length or of varying lengths. Therefore, it is contemplated to construct access assemblies having a combination of slits and protrusions.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure. As well, one skilled in the art will appreciate further features and advantages of the present disclosure based on the above-described embodiments. Accordingly, the present disclosure is not to be limited by what has been particularly shown and described, except as indicated by the appended claims.

The invention claimed is:

1. An access assembly comprising:
   a tubular member having a proximal end and a distal end, the proximal end in mechanical cooperation with at least one slit seal member configured to create a fluid-tight seal in a first configuration;
   a first ring secured at the proximal end of the tubular member; and
   a second ring secured at the distal end of the tubular member;
   wherein the at least one slit seal member is configured to create an opening in a second configuration when radially inward compression forces are applied directly on opposed ends of an exterior surface of the first ring; and
   wherein the at least one slit seal member is transitionable from a linear configuration to an irregular configuration after application of the radially inward compression forces directly on the opposed ends of the exterior surface of the first ring.

2. The access assembly according to claim 1, wherein the first ring is configured to be received external of tissue.

3. The access assembly according to claim 1, wherein the second ring is configured to be received within a body cavity.

4. The access assembly according to claim 1, wherein the tubular member is configured to be tapered in a first position to facilitate insertion through the tissue and is configured to define a substantially hour-glass shape in a second position.

5. The access assembly according to claim 1, wherein the at least one slit seal member is configured to act, in the second configuration, as a smoke vent for enabling smoke evacuation from a surgical site.

6. The access assembly according to claim 1, wherein the at least one slit seal member is configured to receive, in the second configuration, at least one surgical instrument therethrough.

7. The access assembly according to claim 1, wherein the proximal end of the tubular member includes a plurality of lumens.

8. The access assembly according to claim 1, wherein the proximal end of the tubular member includes a plurality of slit seal members.

9. The access assembly according to claim 1, wherein the proximal end of the tubular member includes a plurality of lumens and a plurality of slit seal members.

10. The access assembly according to claim 1, wherein the at least one slit seal member is configured to be in a straight configuration.

11. The access assembly according to claim 1, wherein the at least one slit seal member is constructed as a plurality of parallel slits of successively increasing or decreasing lengths.

12. The access assembly according to claim 1, wherein the at least one slit seal member is configured to be a duckbill protrusion.

13. The access assembly according to claim 1, wherein the proximal end of the tubular member includes a plurality of duckbill protrusions.

14. The access assembly according to claim 1, wherein the proximal end of the tubular member includes at least two slit seal members, one configured to be in a straight configuration and one configured to be a duckbill configuration.

15. A method comprising:
   accessing a body cavity by:
      providing a tubular member having a proximal end and a distal end, the proximal end in mechanical cooperation with at least one slit seal member configured to create a fluid-tight seal in a first configuration;
      securing a first ring at the proximal end of the tubular member; and
      securing a second ring at the distal end of the tubular member;
      wherein the at least one slit seal member is configured to create an opening in a second configuration when radially inward compression forces are applied directly on opposed ends of an exterior surface of the first ring; and
      wherein the at least one slit seal member is transitionable from a linear configuration to a curved configuration after application of the radially inward compression forces directly on the opposed ends of the exterior surface of the first ring.

16. The method according to claim 15, further comprising the step of allowing the at least one slit seal member to act, in the second configuration, as a smoke vent for enabling smoke evacuation from a surgical site.

17. The method according to claim 15, further comprising the step of allowing the at least one slit seal member to receive, in the second configuration, at least one surgical instrument therethrough.

18. The method according to claim 15, wherein the at least one slit seal member is constructed as a plurality of parallel slits of successively increasing or decreasing lengths, the at least one slit seal member configured to receive at least one surgical instrument therethrough.

19. The method according to claim 15, further comprising the step of including a plurality of lumens and a plurality of slit seal members at the proximal end of the tubular member for receiving at least one surgical instrument therethrough.

* * * * *